United States Patent [19]

Iida et al.

[11] 4,454,108

[45] Jun. 12, 1984

[54] PROLONGED-ACTION MULTIPLE-LAYER TABLETS

[75] Inventors: Yoshimitsu Iida, Saitama; Atsuko Yoshizawa, Tokyo; Tatuo Kujirai, Saitama; Toshichika Ogasawara, Tokyo, all of Japan

[73] Assignee: Chugai Seiyaku Kabushiki Kaisha, Tokyo, Japan

[21] Appl. No.: 412,074

[22] Filed: Aug. 27, 1982

[30] Foreign Application Priority Data

Sep. 4, 1981 [JP] Japan ................... 56-138339

[51] Int. Cl.³ .................. A61K 9/24; A61K 9/28; A61K 9/42
[52] U.S. Cl. .................... 424/16; 424/14; 424/19; 424/20; 424/21; 424/22; 424/38; 424/361; 424/362
[58] Field of Search .......... 424/15, 16, 19–22, 424/38, 361, 362

[56] References Cited

U.S. PATENT DOCUMENTS

| | | | |
|---|---|---|---|
| 2,793,979 | 5/1957 | Svedres | 424/22 |
| 2,809,917 | 10/1957 | Hermelin | 424/21 |
| 2,951,792 | 9/1960 | Swintosky | 424/21 |
| 3,034,911 | 5/1962 | McKee et al. | 424/361 |
| 3,048,526 | 8/1962 | Boswell | 424/21 |
| 3,079,303 | 2/1963 | Raff et al. | 424/35 |
| 3,096,248 | 7/1963 | Rudzki | 424/35 |
| 3,146,169 | 8/1964 | Stephenson et al. | 424/15 |
| 3,400,197 | 9/1968 | Lippmann | 424/21 |
| 3,490,742 | 1/1970 | Nichols et al. | 424/361 |
| 3,622,677 | 11/1971 | Short et al. | 424/361 |
| 3,632,778 | 1/1972 | Sheth et al. | 424/361 |
| 3,679,794 | 7/1972 | Bentholm et al. | 424/362 |
| 3,852,421 | 12/1974 | Koyanagi et al. | 424/361 |
| 4,091,205 | 5/1978 | Onda et al. | 424/362 |
| 4,140,755 | 2/1979 | Sheth et al. | 424/21 |
| 4,209,513 | 6/1980 | Torode et al. | 424/361 |
| 4,251,518 | 2/1981 | Moore et al. | 424/361 |
| 4,353,887 | 10/1982 | Hess et al. | 424/21 |
| 4,359,483 | 11/1982 | Kaetsu et al. | 424/21 |
| 4,361,545 | 11/1982 | Powell et al. | 424/22 |
| 4,369,308 | 1/1983 | Trubiano | 424/361 |

FOREIGN PATENT DOCUMENTS

| | | | |
|---|---|---|---|
| 983810 | 2/1965 | United Kingdom | 424/15 |
| 1022171 | 3/1966 | United Kingdom . | |

*Primary Examiner*—Shep K. Rose
*Attorney, Agent, or Firm*—Browdy and Neimark

[57] ABSTRACT

A prolonged-action multiple-layer tablet having an increased rate of dissolution of the active ingredient from a given point of time onward is disclosed. The tablet comprises layer A made of an intimate mixture of a water-insoluble wax that has an-average particle size of 10 μm or less and which is solid at ordinary temperatures, a disintegrator and a binder, and layer B made of an intimate mixture of a water-insoluble wax that has an average particle size of 10 μm or less and which is solid at ordinary temperatures, a disintegrator, a binder and the active ingredient. In the tablet, a quick-release layer containing the active ingredient may be formed on either layer A or B.

9 Claims, No Drawings

PROLONGED-ACTION MULTIPLE-LAYER TABLETS

FIELD OF THE INVENTION

The present invention relates to a prolonged-action multiple-layer tablet having an increased rate of dissolution of the active ingredient from a given point of time onward.

BACKGROUND OF THE INVENTION

Various methods have been proposed for preparing drugs that are capable of maintaining the concentration of the effective ingredient in blood for an extended period of time. In particular, active efforts have been made to prepare orally administered drugs that let the active ingredient be dissolved in a given quantity in digestive tracts. It is possible by the state-of-the-art technology to cause the drug substance to be dissolved at a constant rate, but its absorption rate is decreased as it moves toward the lower part of digestive tracts, so with conventional long lasting drugs for oral administration, there is high possibility that the concentration of the active ingredient in blood is decreased as they move along the digestive tract although they have a constant dissolution rate.

As a result of various studies to solve this problem, the present invention have found the following: (1) if part of a tablet is covered with an inert base having substantially the same disintegration rate, the dissolution of the drug substance is prevented for a certain period after oral administration, and when the tablet reaches a site in the digestive tract where the rate of absorption of the drug substance is decreased, the disintegration of the inert base is completed so as to increase the area of the tablet from which the drug substance is released, hence the amount of the substance to be adsorbed by the digestive tract; (2) the base for making such multiple-layer tablet is preferably a mixture of a water-insoluble wax that is solid at ordinary temperatures, a disintegrator and a binder; and (3) the rate of disintegration of the base can be controlled over an extended period by finely micronizing the water-insoluble wax to an average particle size of 10 μm or less, preferably 5 μm or less, with a jet mill or other suitable means.

SUMMARY OF THE INVENTION

The present invention has been accomplished on the basis of these findings and relates to a prolonged-action multiple-layer tablet having an increased rate of dissolution of the active ingredient from a given point of time onward comprising layer A made of an intimate mixture of a water-insoluble wax that has an average particle size of 10 μm or less and which is solid at ordinary temperatures, a distintegrator and a binder, and layer B made of an intimate mixture of a water-insoluble wax that has an average particle size of 10 μm or less and which is solid at ordinary temperatures, a disintegrator, a binder and the active ingredient.

DETAILED DESCRIPTION OF THE INVENTION

Figure 1:
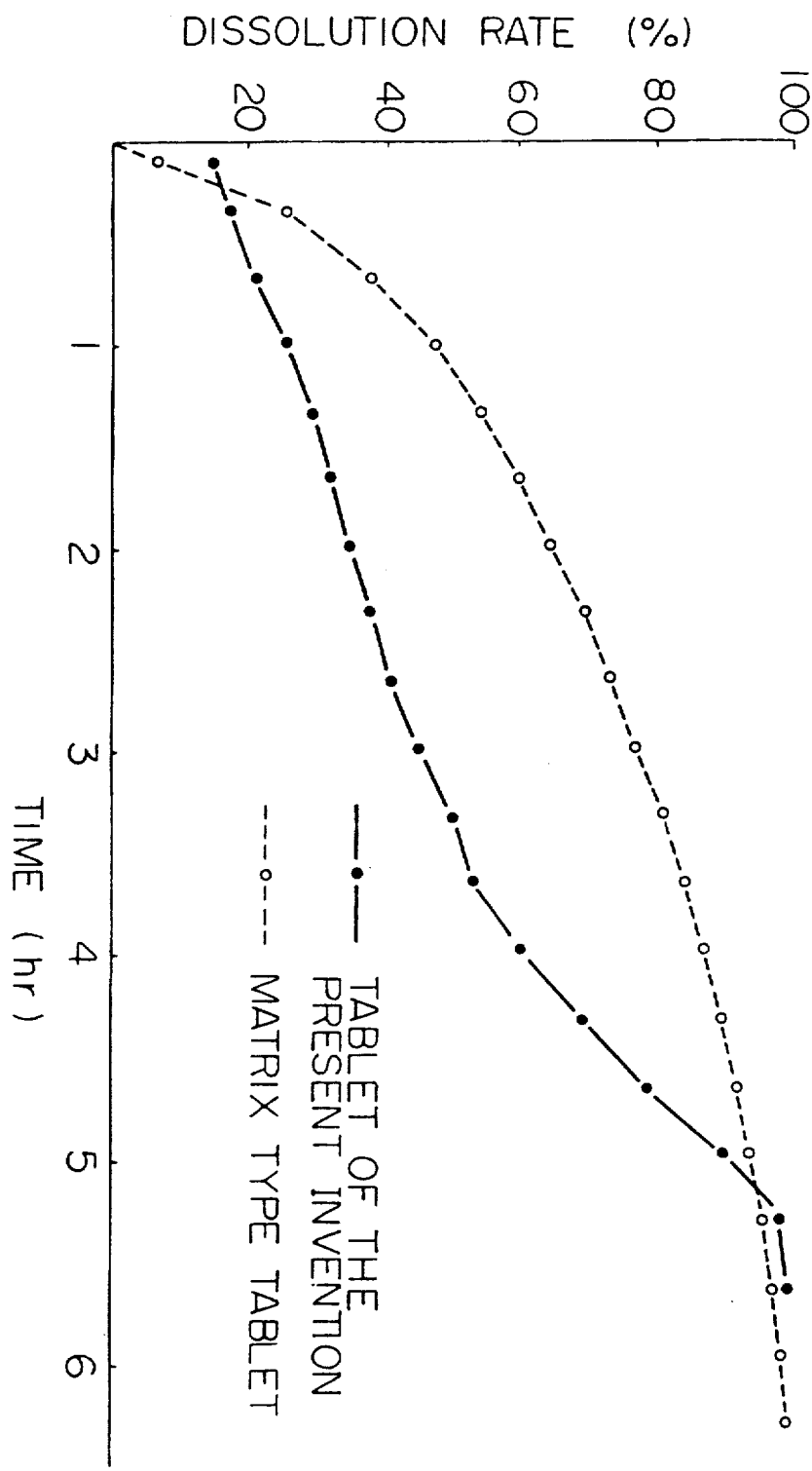

Examples of the water-insoluble wax that is solid at ordinary temperatures include hydrogenated castor oil, hydrogenated soybean oil, carnauba wax, parrffin, palmitic acid, stearic acid, bees wax, stearyl alcohol and octadecyl alcohol. Examples of the disintegrator include low-substituted hydroxypropyl cellulose, carboxymethyl cellulose, calcium carboxymethyl cellulose, sodium carboxymethyl cellulose, corn starch, sodium starch glycolate, and hydroxypropyl starch. The disintegrator is used in an amount of from 0.5 to 40% (w/w), preferably from 1 to 20% (w/w). Any compound can be used as the binder if it dissolves or is digested in the digestive tract, and illustrative examples include hydroxypropyl cellulose, hydroxypropylmethyl cellulose, hydroxypropylmethyl cellulose phthalate, gelatin, α-starch, polyvinyl pyrrolidone and polyethylene glycol. The binder is used in an amount of from 0.1 to 30% (w/w), preferably from 0.5 to 15% (w/w). The binder is used as a solution in a suitable solvent. Needless to say, a suitable coloring agent, lubricant, flavoring agent and diluent may be incorporated in the tablet of the present invention as required.

EXAMPLE 1

Hydrogenated castor oil (Lubriwax 101 from Freund Inc. Co., Ltd.) was micronized into fine particles of a mean size of 1.5 μm (as measured by the centrifugal sedimentation method) with a micro jet mill (Model FS-4 of Seishin Enterprise Co., Ltd., Japan). Ninety grams of the particles was intimately mixed with 8 g of low-substituted hydroxypropyl cellulose (L-HPC.LH-31 from Shinetsu Chemical Co., Ltd., Japan) in a mortar. The mixture was kneaded well with 20 g of a 10% (w/w) aqueous solution of hydroxypropyl cellulose (HPC-L from Nihon Soda Co., Ltd., Japan) and 43 g of pure water. The blend was sifted through a 20 mesh sieve into a granulation which was dried in a tray drier at 50° C. for 5 hours. Then, the granulation was classified through a 14 mesh sieve and the product was referred to as granulation (a).

Granulation (a) (42.5 g) and 7.5 g of a nitrate ester of N-(2-hydroxyethyl)nicotinic acid amide that had been screened through a 35 mesh sieve were intimately mixed in a polyethylene bag to form granules which were referred to as granulation (b).

Lactose (5.9 g), 3 g of crystalline cellulose, 0.1 g of calcium stearate and 1 g of a nitrate ester of N-(2-hydroxyethyl)nicotinic acid amide that had been screened through a 35 mesh sieve were intimately mixed in a polyethylene bag to form a powder which was referred to as powder (c).

A single-punch machine with a 10 mmφ die and a flat-face punch was used to make tablets. First, the die was filled with 80 mg of granulation (a) which was given a light stroke of precompression. The die was further filled with 200 mg of granulation (b) which was also given a light stroke of precompression. Then, the die was filled with 30 mg of powder (c) which together with the first and second fills was compacted under a total pressure of about 1 ton into a tablet.

For comparison, matrix type tablets were prepared by the conventional method using ethyl cellulose. Each tablet (310 mg) contained 33 mg of a nitrate ester of N-(2-hydroxyethyl)nicotinic acid amide.

Figure 2:
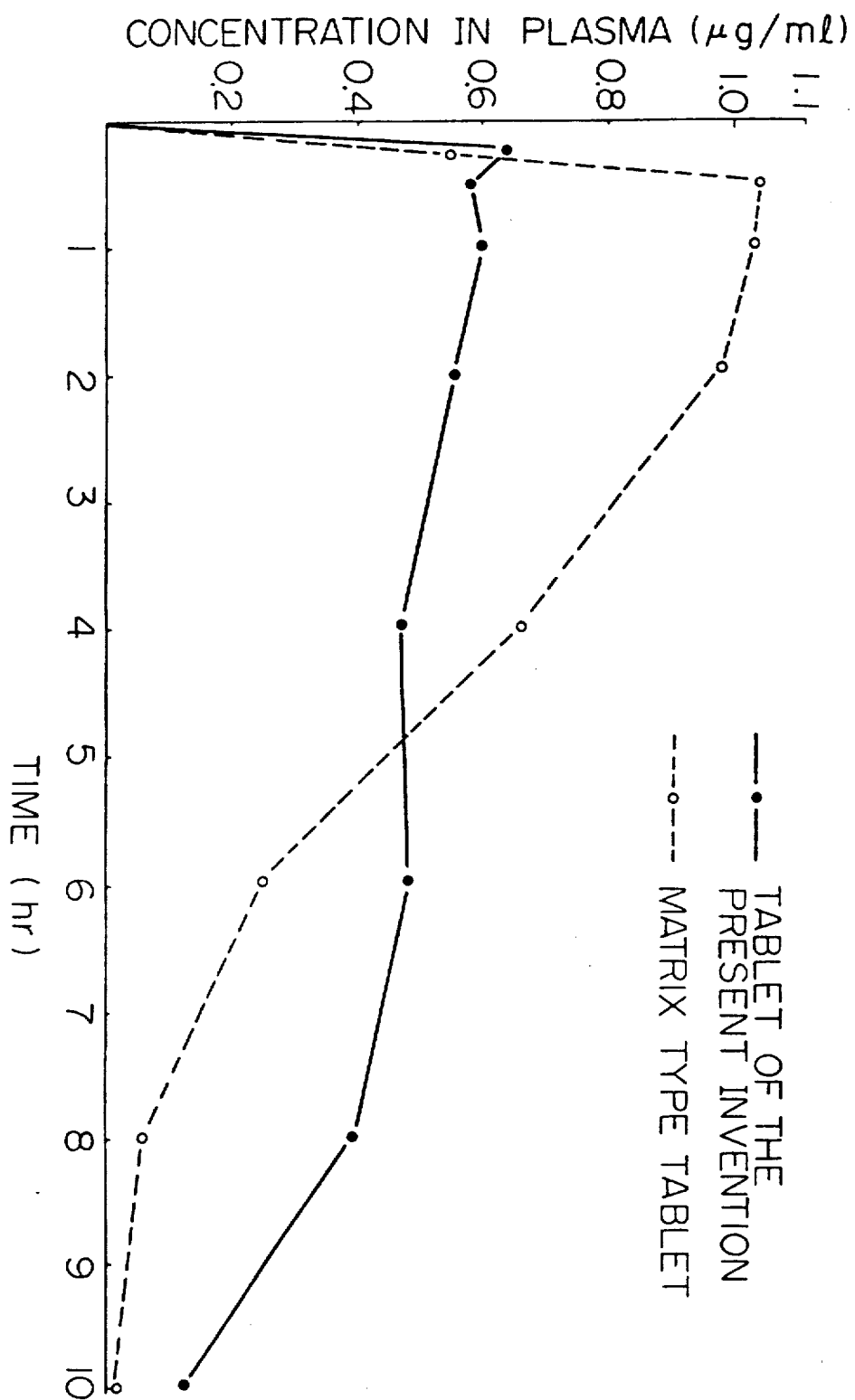

The profile of dissolution of the two kinds of tablet is shown in FIGS. 1 and 2. FIG. 1 is the dissolution rate vs. time curve for a solution having a pH of 6.8. FIG. 2 is the average concentration of the active ingregient in plasma vs. time curve when the tablets were administered to 6 beagles.

EXAMPLE 2

Carnauba wax was micronized into fine particles of a mean size of 2.2 μm (as measured by the centrifugal sedimentation method) with a micro jet mill (Model FS-4 of Seishin Enterprise Co., Ltd.). A hundred and forty grams of the particles was intimately mixed with 6 g of calcium carboxymethyl cellulose (ECG-505 from Gotoku Yakuhin Kogyo, Japan) and 50 g of acetyl salicyclic acid in a mortar. The mixture was kneaded well with 100 g of a 4% solution of hydroxypropylmethyl cellulose (60SH-50 from Shinetsu Chemical Co., Ltd.) in 50% ethanol. The blend was granulated with a rotary granulator having a 0.8 mmφ net. The granulation was dried in a fluid-bed dryer at 60° C. for 20 minutes and classified through a 14 mesh sieve. The resulting product was referred to as granulation (a).

Stearic acid was micronized into fine particles of a mean size of 2.9 μm (as measured by the centrifugal sedimentation method) with a micro jet mill (Model FS-4 of Seishin Enterprise Co., Ltd.). Eighty-four grams of the particles was intimately mixed with 4 g of carboxymethyl cellulose (NS-300 from Gotoku Yakuhin Kogyo) and 10 g of mannitol in a mortar. The mixture was kneaded well with 50 g of a 4% solution of hydroxypropyl cellulose (HPC-M of Nihon Soda Co., Ltd.) in 50% ethanol. The blend was granulated with a rotary granulator having a 0.8 mmφ net. The granulation was dried with a fluid-bed dryer at 50° C. for 40 minutes, and classified through a 14 mesh sieve. The resulting product was referred to as granulation (b).

A single punch machine with a 10 mmφ die and a flat-face bevel-edge punch with a score line was used to make tablets. First, the die was filled with 200 mg of granulation (a) which was given a light stroke of precompression. The die was then filled with 100 mg of granulation (b) which together with the first fill was compacted under a total pressure of about 1 ton into a tablet.

Figure 3:
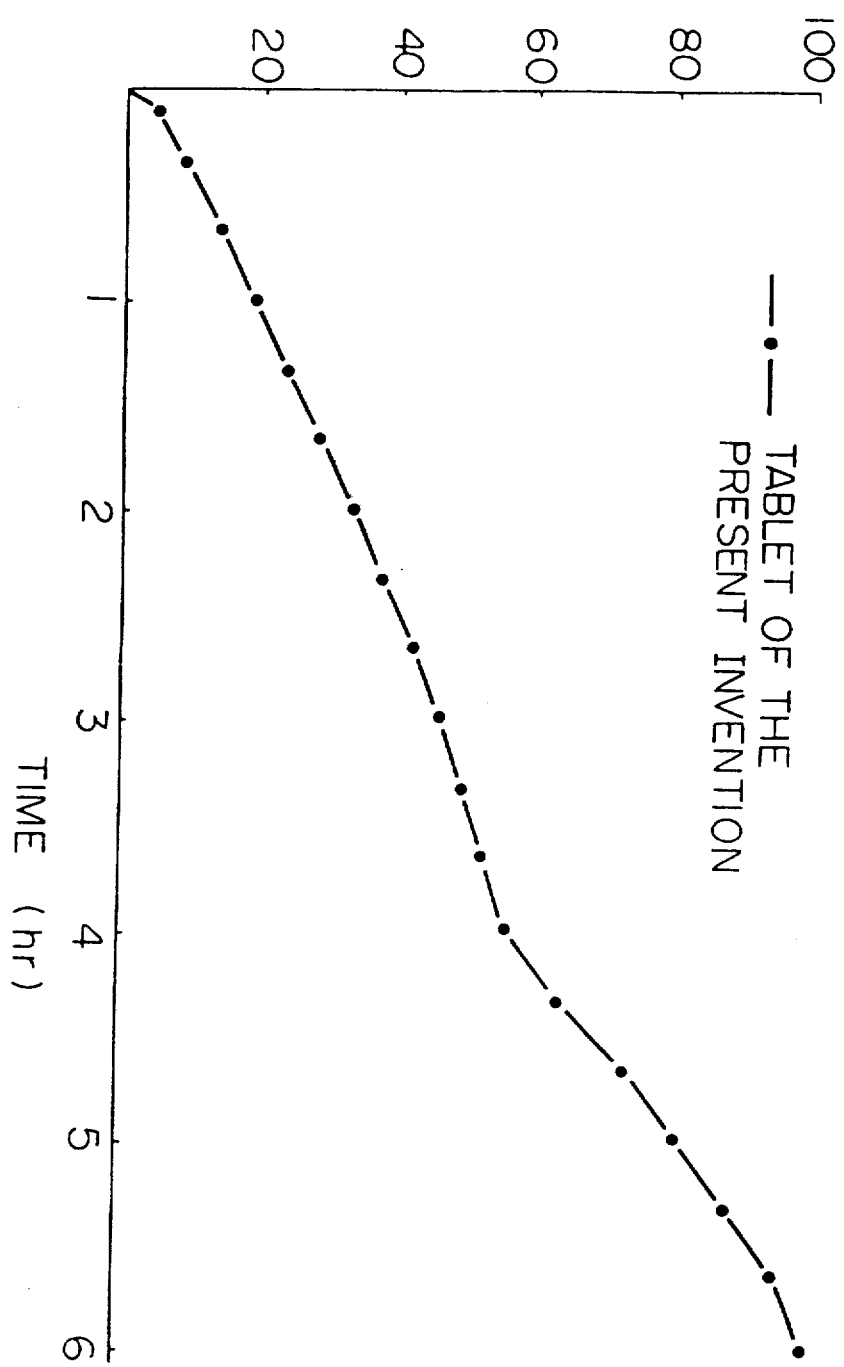
Figure 4:
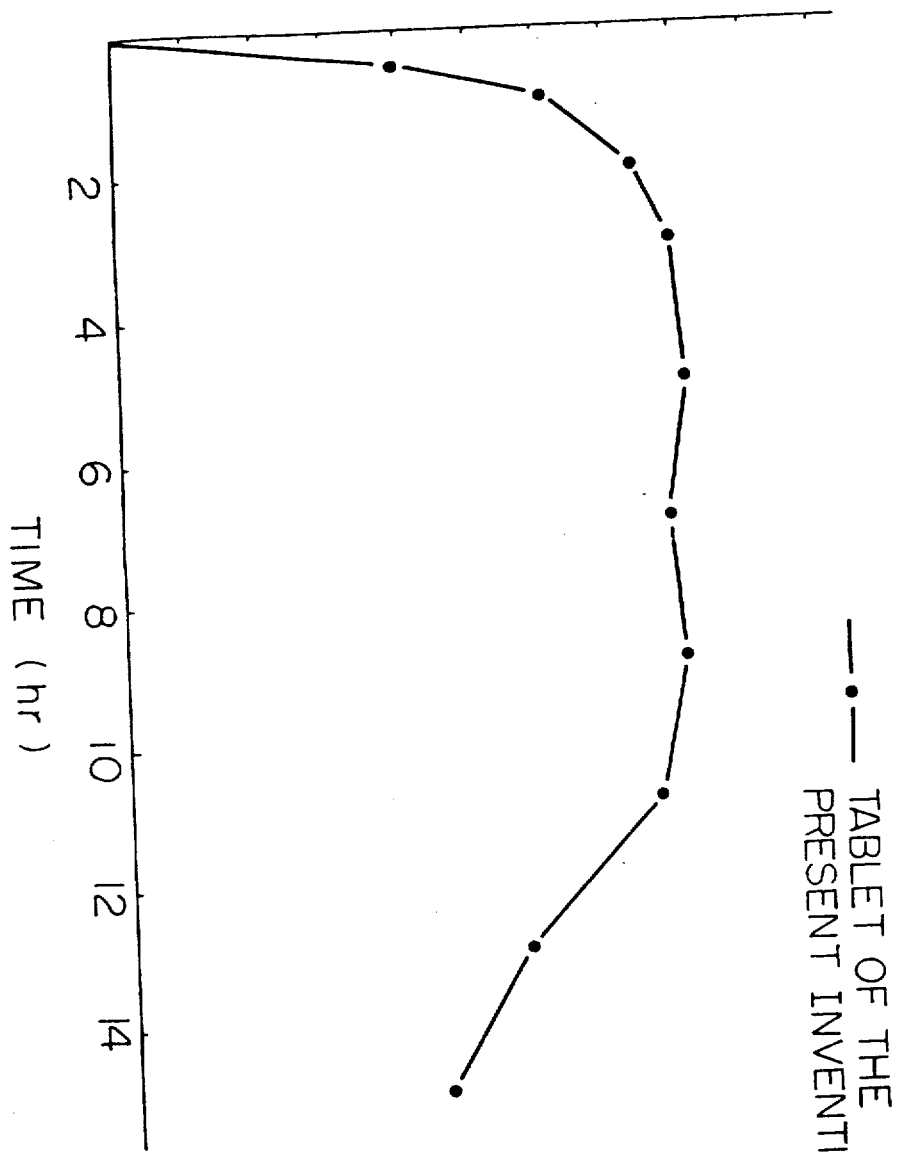

The profile of dissolution of the tablets so prepared is shown in FIGS. 3 and 4. FIG. 3 is the dissolution rate vs. time curve for a solution having a pH of 6.8. FIG. 4 is the average concentration of the active ingredient in plasma vs. time curve when five tablets were administered to 4 beagles.

EXAMPLE 3

Hydrogenated soybean oil (Lubriwax 102H from Freund Inc. Co., Ltd.) was micronized into fine particles of a mean size of 3.1 μm (as measured by the centrifugal sedimentation method) with a micro jet mill (Model FS-4 of Seishin Enterprise Co., Ltd.). Sixty-six grams of the particles was intimately mixed with 12 g of low-substituted hydroxypropyl cellulose (L-HPC.LH-31 from Shinetsu Chemical Co., Ltd.) and 10 g of ethyl 7-[4-(2-methoxyphenyl)-1-piperazino]-heptanoate monofumarate in a mortar. The blend was kneaded well with 40 g of a 30% (w/w) aqueous solution of hydroxypropyl cellulose (HPC-SL of Nihon Soda Co., Ltd.). The blend was sifted through a 20 mesh sieve into a granulation which was dried in a tray drier at 50° C. for 5 hours. Then, the granulation was classified through a 14 mesh sieve and the product was referred to as granulation (a).

Hydrogenated soybean oil (Lubriwax 102H from Freund Inc. Co., Ltd.) was micronized into fine particles with a micro jet mill (Model FS-4 of Seishin Enterprise Co., Ltd.), and 76 g of the particles was intimately mixed with 12 g of low-substituted hydroxypropyl cellulose (L-HPC.LH-31 from Shinetsu Chemical Co., Ltd.) in a mortar. The blend was kneaded well with 40 g of a 30% (w/w) aqueous solution of hydroxypropyl cellulose (HPC-SL from Nihon Soda Co., Ltd.) and 3 g of pure water. The blend was sifted through a 20 mesh sieve into a granulation which was dried in a tray drier at 50° C. for 5 hours. Then, the granulation was classified through a 14 mesh sieve and the product was referred to as granulation (b).

A single-punch machine with a 10 mmφ die and a standard 13 R punch was used to make tablets. First, the die was filled with 200 mg of granulation (a) which was given a light stroke of precompression. The die was then filled with 100 mg of granulation (b) which together with the first fill was compacted under a total pressure of about 1 ton into a tablet.

For comparison, multiple-layer tablets were prepared by the same method except that the hydrogenated soybean oil was not finely micronized and had a particle size of 20 to 80 μm as measured under a microscope.

Figure 5:
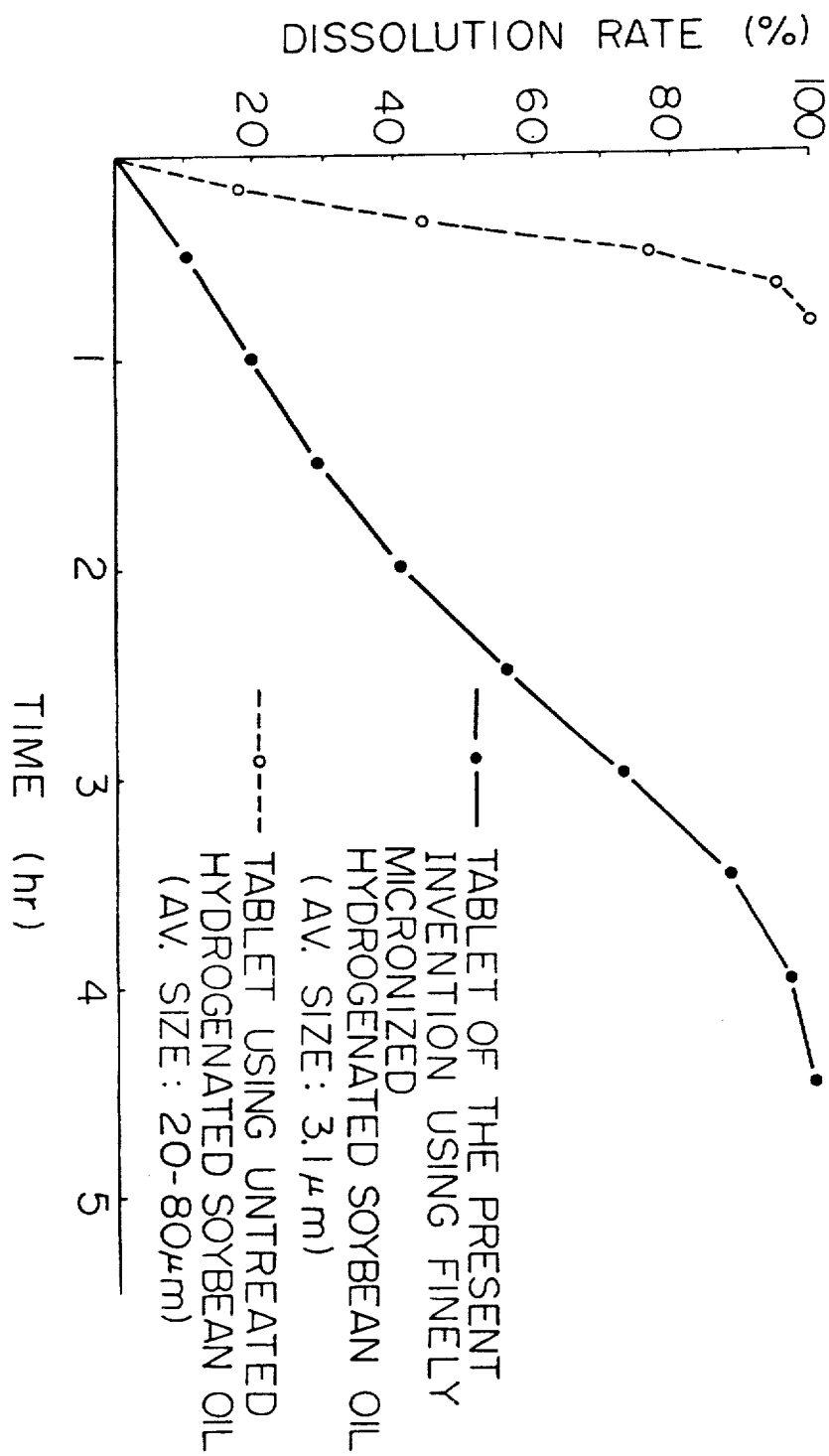

The profile of dissolution of the two kinds of tablet is shown in FIGS. 5 and 6. FIG. 5 is the dissolution rate vs. time curve for a solution having a pH of 2.2. FIG. 6 depicts a curve for time vs. average concentration of metabolite 1-(6-carboxylhexyl)-4-(o-methoxyphenyl)-piperazine in plasma when each tablet was administered to 6 beagles.

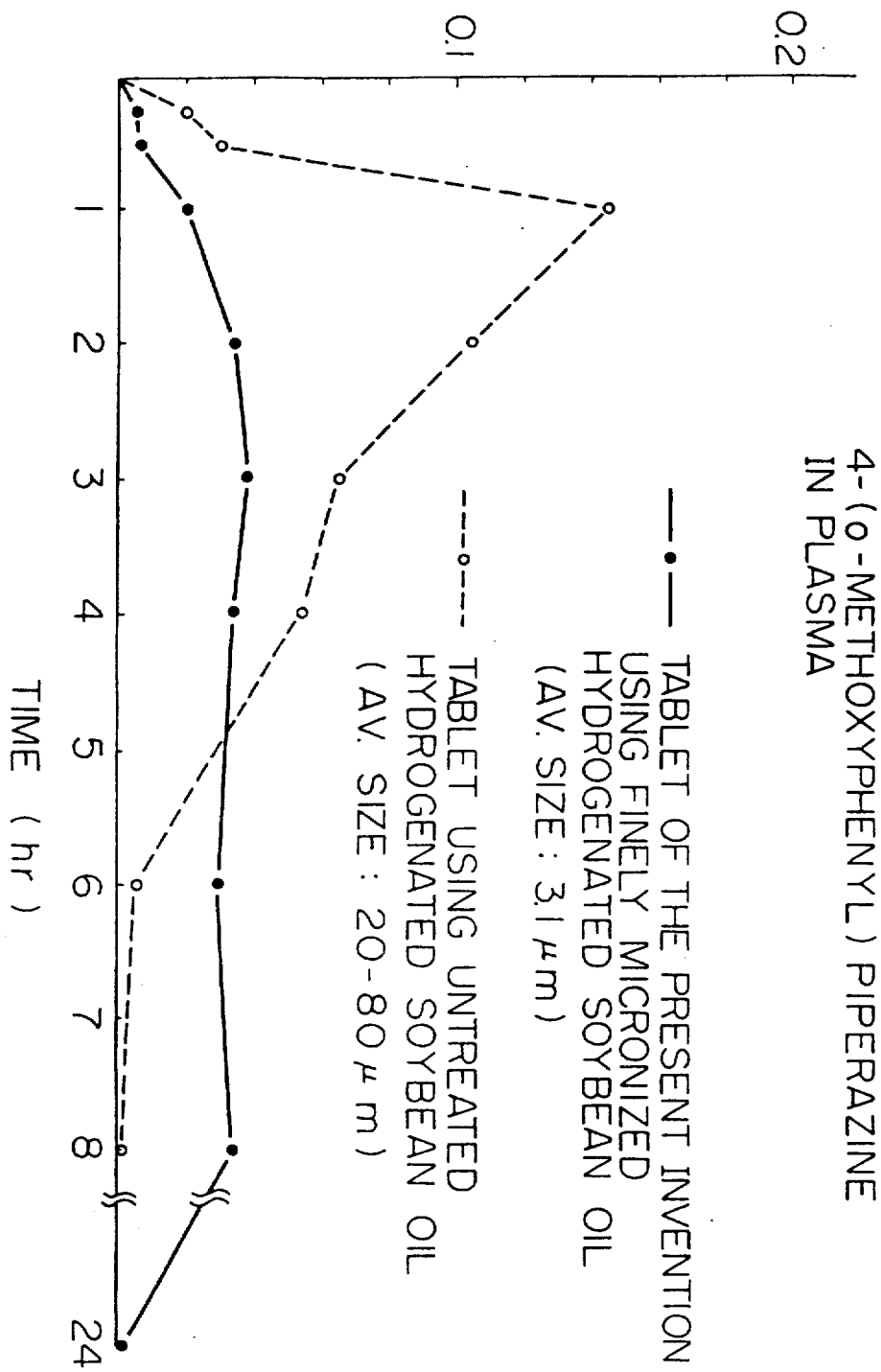

What is claimed is:

1. A prolonged-action multiple-layer tablet having an increased rate of dissolution of the active ingredient from a given point of time onward, comprising
    an inert layer A made of an intimate mixture of a water-insoluble wax that has an average particle size of 10 μm or less and which is solid at ordinary temperatures, selected from the group consisting of hydrogenated castor oil, hydrogenated soybean oil, carnauba wax, paraffin, palmitic acid, stearic acid, bees wax, stearyl alcohol, and octadecyl alcohol,
    a disintegrator selected from the group consisting of low-substituted hydroxypropyl cellulose, carboxymethyl cellulose, calcium carboxymethyl cellulose, sodium carboxymethyl cellulose, corn starch, sodium starch glycolate and hydroxypropyl starch,
    and a binder selected from the group consisting of hydroxypropyl cellulose, hydroxypropylmethyl cellulose, hydroxypropylmethyl cellulose phthalate, gelatin, α-starch, polyvinyl pyrrolidone and polyethylene glycol; and
    layer B made of an intimate mixture of a said water-insoluble wax that has an average particle size of 10 μm or less and which is solid at ordinary temperatures, a said disintegrator, a said binder and the active ingredient and wherein layer B covers part of layer A, and layer A covers part of layer B.

2. A tablet according to claim 1 wherein a quick-release layer containing the active ingredient is formed on either layer A or B.

3. A tablet according to claim 1 wherein the water-insoluble wax which is solid at orindary temperatures has an average size of 5 μm or less.

4. A tablet according to claim 1 wherein the disintegrator is contained in an amount of from 0.5 to 40% (w/w).

5. A tablet according to claim 1 wherein the disintegrator is contained in an amount of from 1 to 20% (w/w).

6. A tablet according to claim 1 wherein the binder is contained in an amount of from 0.1 to 30% (w/w).

7. A tablet according to claim 1 wherein the binder is contained in an amount of from 0.5 to 15% (w/w).

8. A tablet according to claim 1 wherein the active ingredient is selected from among a nitrate ester of N-(2-hydroxyethyl)nicotinic acid amide, acetyl salicylic acid and ethyl 7-[4-(2-methoxyphenyl)-1-piperazino]-heptanoate.

9. A tablet according to claim 1, wherein the quantity and thickness of layer B is greater than the quantity and thickness of layer A.

* * * * *

UNITED STATES PATENT AND TRADEMARK OFFICE
CERTIFICATE OF CORRECTION

PATENT NO. : 4,454,108
DATED : June 12, 1984
INVENTOR(S) : Yoshimitsu Iida et al.

It is certified that error appears in the above-identified patent and that said Letters Patent is hereby corrected as shown below:

The sheets of drawings consisting of Figs. 1, 2, 3, 4, 5, and 6 should be added as shown on the attached sheets.

On the title page, "9 Claims, No Drawings" should read -- 9 Claims, 6 Drawing Figures --.

Signed and Sealed this

Eighteenth Day of March 1986

[SEAL]

Attest:

DONALD J. QUIGG

Attesting Officer     Commissioner of Patents and Trademarks